(12) United States Patent
Ivosevic

(10) Patent No.: US 11,213,232 B2
(45) Date of Patent: Jan. 4, 2022

(54) DEVICE FOR TRAPPING AN INITIAL FLOW OF BLOOD

(71) Applicant: BECTON DICKINSON AND COMPANY, Franklin Lakes, NJ (US)

(72) Inventor: Milan Ivosevic, Kinnelon, NJ (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 51 days.

(21) Appl. No.: 16/631,353

(22) PCT Filed: Jul. 17, 2018

(86) PCT No.: PCT/US2018/042367
§ 371 (c)(1),
(2) Date: Jan. 15, 2020

(87) PCT Pub. No.: WO2019/018324
PCT Pub. Date: Jan. 24, 2019

(65) Prior Publication Data
US 2020/0214611 A1 Jul. 9, 2020

Related U.S. Application Data

(60) Provisional application No. 62/533,288, filed on Jul. 17, 2017.

(51) Int. Cl.
*A61B 5/15* (2006.01)
*A61B 5/154* (2006.01)
*A61B 5/155* (2006.01)

(52) U.S. Cl.
CPC ........ *A61B 5/15003* (2013.01); *A61B 5/1405* (2013.01); *A61B 5/1427* (2013.01);
(Continued)

(58) Field of Classification Search
CPC .......... A61B 5/15003; A61B 5/150213; A61B 5/150305; A61B 5/150732; A61B 5/1545; A61B 5/15074
See application file for complete search history.

(56) References Cited

U.S. PATENT DOCUMENTS 6,315,738 B1 * 11/2001 Nishikawa ....... A61B 5/150213
600/583
2009/0227896 A1 9/2009 Tan et al.
(Continued)

FOREIGN PATENT DOCUMENTS

EP 1602328 A1 12/2005

OTHER PUBLICATIONS

PCT International Search Report issued in corresponding PCT application No. PCT/US2018/042367 dated Oct. 30, 2018.

*Primary Examiner* — Sean P Dougherty
*Assistant Examiner* — Alexander H Connor
(74) *Attorney, Agent, or Firm* — Botos Churchill IP Law LLP

(57) ABSTRACT

Various embodiments of the present disclosure describe a diversion device that traps an initial flow of blood in a diversion chamber of the diversion device. The diversion chamber may be defined, in part, by a housing shell, a housing base, and a filter. The filter may be a porous material that allows air, but not blood, to flow through it. After the diversion chamber is filled, a subsequent flow of blood may be directed into a collection vessel through an internal conduit of the diversion device.

20 Claims, 10 Drawing Sheets

(52) U.S. Cl.
CPC ...... *A61B 5/1545* (2013.01); *A61B 5/150213* (2013.01); *A61B 5/150305* (2013.01); *A61B 5/150732* (2013.01)

(56) References Cited

U.S. PATENT DOCUMENTS

| | | | |
|---|---|---|---|
| 2009/0227953 A1* | 9/2009 | Tan | A61B 5/150488 604/168.01 |
| 2016/0354020 A1* | 12/2016 | Anitua Aldecoa | A61B 5/15003 |
| 2017/0020427 A1* | 1/2017 | Rogers | A61B 5/15003 |
| 2018/0271425 A1* | 9/2018 | Rogers | A61B 5/153 |
| 2018/0353117 A1* | 12/2018 | Bullington | A61B 5/15003 |
| 2019/0374145 A1* | 12/2019 | Breindel | A61B 5/150251 |

* cited by examiner

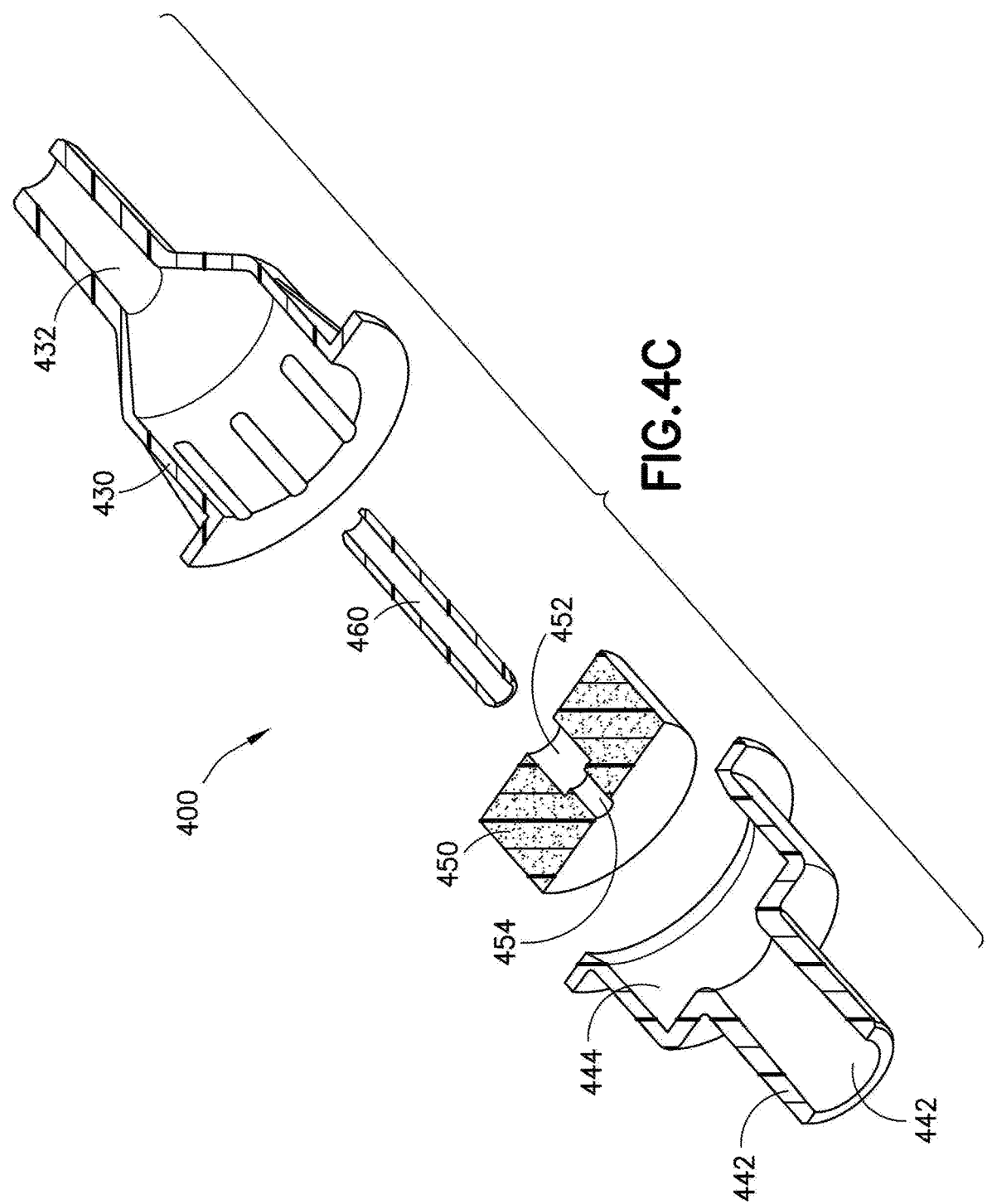

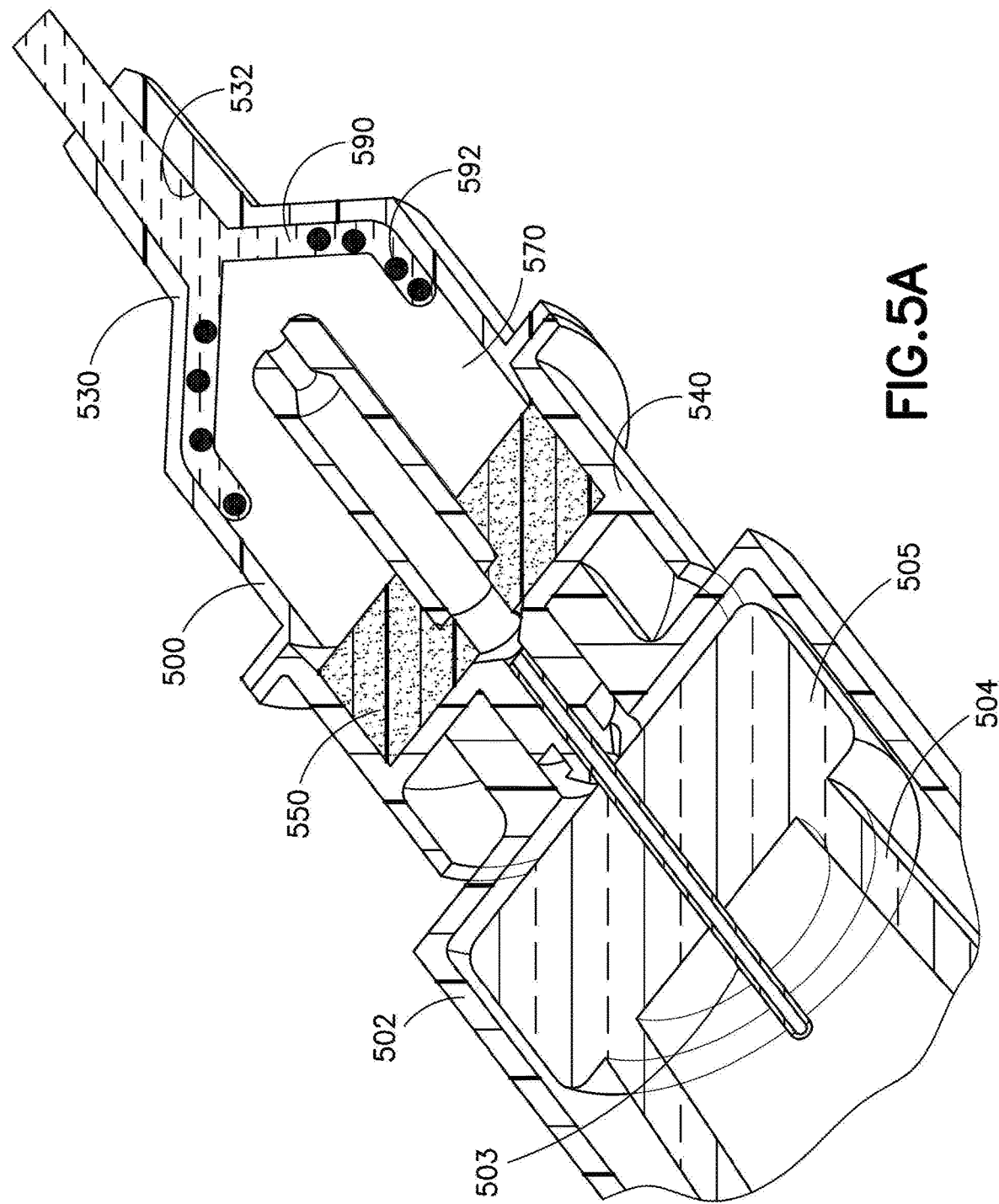

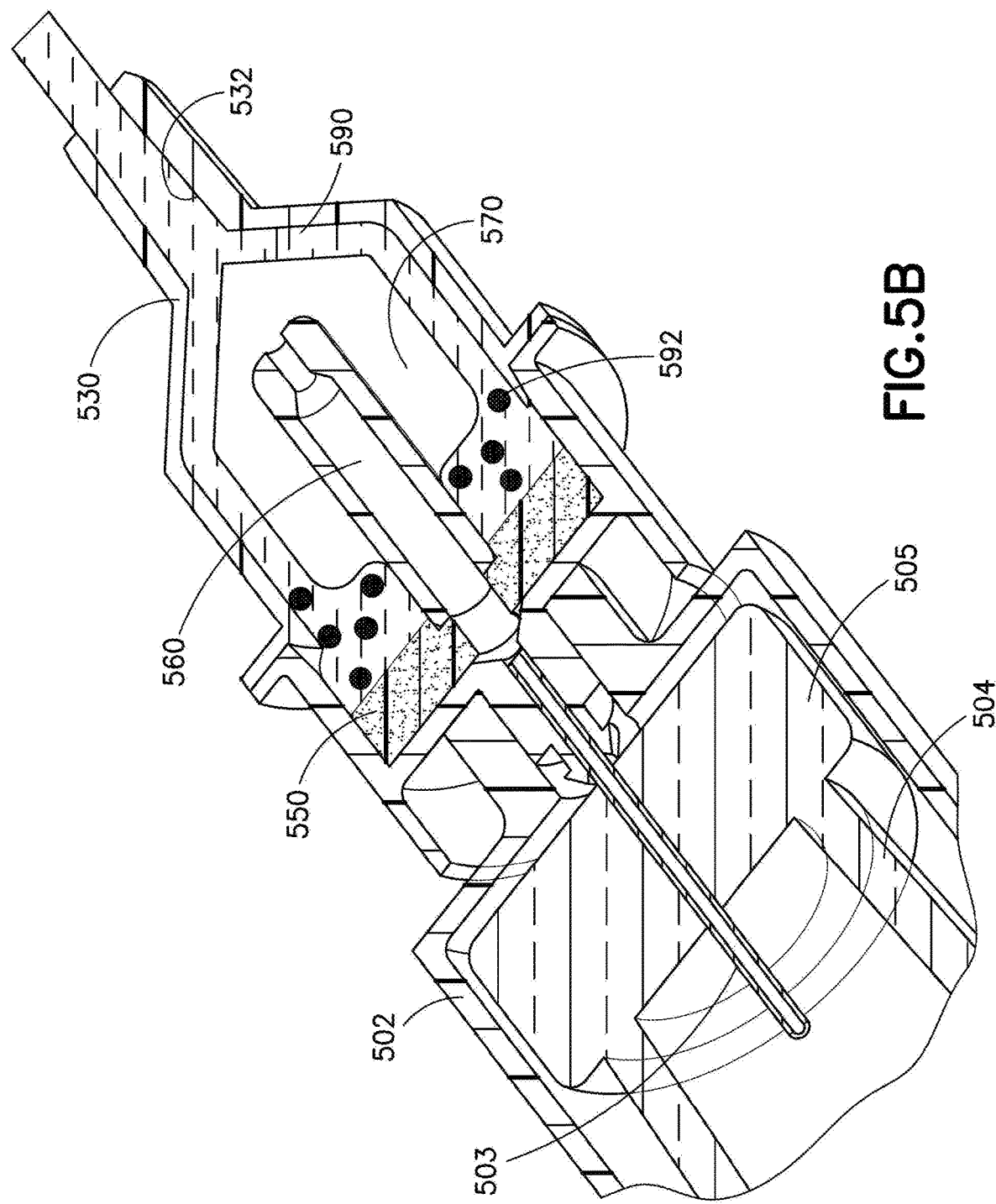

DEVICE FOR TRAPPING AN INITIAL FLOW OF BLOOD

CROSS-REFERENCE TO RELATED APPLICATIONS

The present application is a national phase entry under 35 U. S. C. § 371 of International Application No. PCT/US2018/042367, filed Jul. 17, 2018, which claims the benefit of the filing date of U.S. Provisional Patent Application No. 62/533,288, filed Jul. 17, 2017, the disclosures of which hereby incorporated herein by reference.

TECHNICAL FIELD

The present technology relates to a device for trapping an initial flow of blood during a blood collection process.

BACKGROUND

A blood culture test is presently the preferred method for identifying bacteremia and septicemia (sepsis). Sepsis is a body-wide response to a bacterial infection of the blood stream that can cause organ failure and death. Sepsis kills every one in six infected patients. Moreover, half of all in-hospital deaths involve sepsis. In fact, sepsis kills more people than AIDS, breast cancer and prostate cancer combined. Sepsis affects more hospital patients than any other diagnosis.

Unfortunately, the United States healthcare system spends over $4 billion each year on unnecessary treatment associated with false positive blood culture results. See Oren Zwang & Richard K. Albert, *Analysis of Strategies to Improve Cost Effectiveness of Blood Cultures*, 1 J. Hosp. Med. 272 (September 2006). Moreover, "[i]t is currently accepted that most organisms identified as contaminants in blood cultures originate from the skin of the patient." Robert A. Garcia et al., *Multidisciplinary Team Review of Best Practices for Collection and Handling of Blood Cultures to Determine Effective Interventions for Increasing the Yield of True-Positive Bacteremia, Reducing Contamination, and Eliminating False Positive Central Line Associated Bloodstream Infections*, 43 Am. J. Infect. Control 1222 (November 2015).

Thus, during a blood collection process, there is a need for a device capable of diverting and trapping an initial flow of blood from a patient that might contain contaminants from the skin of that patient in order to reduce the number of false positives.

BRIEF SUMMARY

Various embodiments of the present disclosure describe a diversion device that traps an initial flow of blood in a diversion chamber of the diversion device. The diversion chamber may be defined, in part, by a housing shell, a housing base, and a filter. The filter may be a porous material that allows air, but not blood, to flow through it. After the diversion chamber is filled, a subsequent flow of blood may be directed into a collection vessel through an internal conduit of the diversion device.

One aspect of the present disclosure relates to a diversion device comprising: (1) a housing having an inlet conduit and an outlet conduit, wherein the housing is configured to receive an initial flow of blood and a subsequent flow of blood through the inlet conduit, and wherein the housing is configured to allow the subsequent flow of blood to exit the diversion device through the outlet conduit; (2) a filter positioned within the housing adjacent to the outlet conduit, wherein the filter comprises a material that allows air, but not blood, to pass through it; (3) a diversion chamber defined by portions of the housing and the filter, wherein the diversion chamber is configured to receive and retain the initial flow of blood; and (4) an internal conduit positioned within the housing, wherein the internal conduit is configured to permit the subsequent flow of fluid to exit the diversion device.

In some embodiments, a portion of the housing comprises a hydrophilic material. In some embodiments, a portion of the internal conduit comprises a hydrophobic material. In some embodiments, the internal conduit extends into the diversion chamber, and a cross-sectional area of the diversion chamber is larger than a cross-sectional area of the internal conduit. In some embodiments, the internal conduit comprises a tube and a conduit formed in the filter, and a portion of the tube is positioned within a tube receptacle formed in the filter. In some embodiments, the housing comprises a housing shell and a housing base, wherein the housing shell contains the inlet conduit, wherein the housing base contains the outlet conduit, and wherein the filter is positioned within a filter receptacle formed in the housing base. In some embodiments, the filter comprises a hydrophilic material. In some embodiments, the hydrophilic material is carboxymethylcellulose ("CMC"). In some embodiments, a vacuum pressure created by a collection vessel coupled to the diversion device draws the initial flow of blood into the diversion chamber. In some embodiments, the internal conduit is configured to permit the subsequent flow of fluid to exit the diversion device using only the vacuum pressure created by the collection vessel coupled to the diversion device.

Another aspect of the present disclosure relates to a blood collection kit comprising: instructions to assemble a blood collection pathway from a patient to a collection vessel, wherein the blood collection pathway comprises a first needle piercing the skin of the patient and a diversion device, and wherein the collection vessel has a sub-atmospheric internal pressure that draws (a) an initial flow of blood from the patient through the first needle and into the diversion device and (b) a subsequent flow of blood through the first needle and the diversion device, respectively, and into the collection vessel, and wherein the blood collection pathway is a closed system that prevents an initial flow of air through the diversion device from being vented into the atmosphere.

In some embodiments, the blood collection pathway further comprises a holder having a second needle piercing a cap of the collection vessel. In some embodiments, the diversion device is integrated with the holder. In some embodiments, the diversion device and the holder are separate units. In some embodiments, the collection vessel contains one or more a bacterial growth media, an antibiotic scavenger, or a pH sensor.

Yet another aspect of the present disclosure relates to a blood collection method comprising: assembling a blood collection pathway from a patient to a collection vessel, wherein the blood collection pathway comprises a first needle piercing the skin of the patient and a diversion device, and wherein the collection vessel has a sub-atmospheric internal pressure that draws (a) an initial flow of blood from the patient through the first needle and into the diversion device and (b) a subsequent flow of blood through the first needle and the diversion device, respectively, and into the collection vessel, and wherein the diversion device comprises: (1) a housing having an inlet conduit and an outlet conduit, wherein the housing is configured to receive an initial flow of blood and a subsequent flow of blood through the inlet conduit, and wherein the housing is configured to allow the subsequent flow of blood to exit the diversion device through the outlet conduit; (2) a filter positioned within the housing adjacent to the outlet conduit, wherein the filter comprises a material that allows air, but not blood, to pass through it; (3) a diversion chamber defined by portions of the housing and the filter, wherein the diversion chamber is configured to receive and retain the initial flow of blood; and (4) an internal conduit positioned within the housing, wherein the internal conduit is configured to permit the subsequent flow of fluid to exit the diversion device.

In some embodiments, the blood collection pathway is a closed system that prevents an initial flow of air through the diversion device from being vented into the atmosphere. In some embodiments, the blood collection pathway further comprises a holder having a second needle piercing a cap of the collection vessel. In some embodiments, the diversion device is integrated with the holder. In some embodiments, the diversion device and the holder are separate units.

BRIEF DESCRIPTION OF DRAWINGS

FIG. 4C is an exploded diagram of the cross-sectional view of FIG. 4B.

FIG. 5A illustrates how an initial flow of blood may flow into a diversion chamber of a diversion device in accordance with the present technology.

FIG. 5B illustrates how an initial flow of blood may begin to fill the diversion chamber of the diversion device of FIG. 5A.

DETAILED DESCRIPTION

Figure 1:
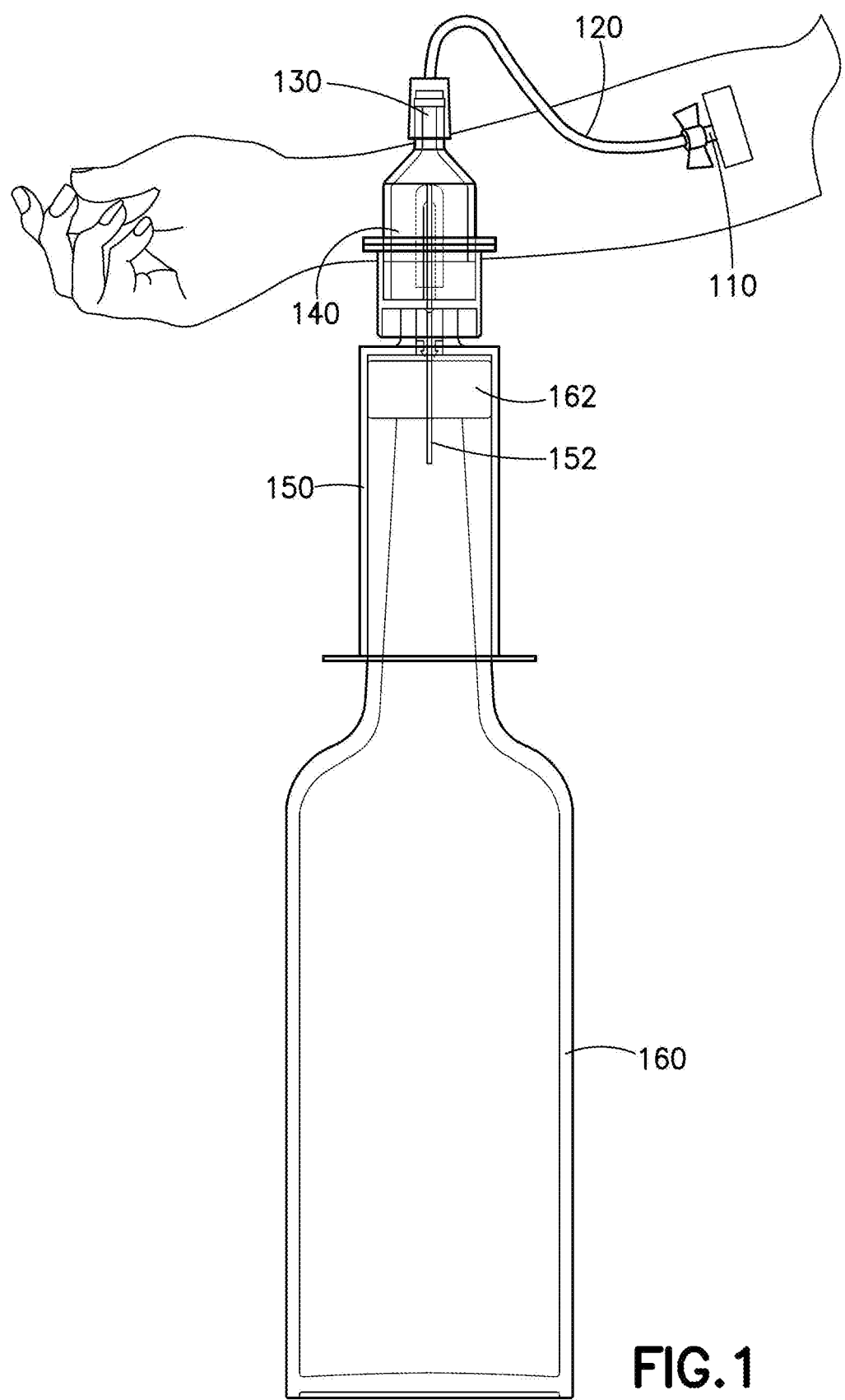
FIG. 1 illustrates a blood collection system comprising one embodiment of a diversion device in accordance with the present technology.

Embodiments of the present disclosure are described in detail with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

FIG. 1 illustrates a blood collection system comprising one embodiment of a diversion device in accordance with the present technology. As shown in FIG. 1, the blood collection system includes Needle 110, Tubing 120, Adapter 130, Diversion Device 140, Holder 150, and Collection Bottle 160. Holder 150 includes Needle 152. Collection Bottle includes Cap 162. As shown, Needle 152 has pierced through Cap 162. During the process of collecting a blood sample from a patient, Needle 110 is used to pierce a vein or an artery of the patient. Driven by the vacuum pressure created by Collection Bottle 160, blood from the patient is directed toward Collection Bottle 160 through Tubing 120. An initial flow of blood passes through Adapter 130 and is trapped in a diversion chamber within Diversion Device 140. A subsequent flow of blood is collected in Collection Bottle 160. Along the way, the subsequent flow of blood passes through Adapter 130, Diversion Device 140, and Needle 152.

In some embodiments, the blood collection system of FIG. 1 may be implemented using one of Becton, Dickinson and Company's ("BD's") Vacutainer® blood collection sets, such as BD's Vacutainer® push button blood collection set, BD's Vacutainer® Safety-Lok™ blood collection set, or BD's Vacutainer® UltraTouch™ push button blood collection set. Therefore, in some embodiments, Adapter 130 may be implemented using BD's Vacutainer® Multiple Sample Luer Adapter. Moreover, in some embodiments, Holder 150 may be implemented using BD's Vacutainer® One Use Holder.

As shown in FIG. 1, Diversion Device 140 is integrated with Holder 150. However, in other embodiments, Diversion Device 140 may be a separate unit. Moreover, the size of Diversion Device 140 may be changed to adjust the amount of blood that is initially directed into the diversion chamber within Diversion Device 140. For example, in some embodiments, Diversion Device 140 may be configured to direct 1 mL of blood into its diversion chamber. However, in other embodiments, Diversion Device 140 may be configured to direct 0.5 mL of blood into its diversion chamber. In some embodiments, Diversion Device 140 may include an indicator for providing feedback relating to the amount of collected blood. For example, Diversion Device 140 may include a flow meter that indicates how much blood has been collected inside Collection Bottle 160. The flow meter could minimize potentially false negative blood cultures by helping to ensure that health care workers collect an adequate amount of blood. Furthermore, in some embodiments, a transmitter may be communicatively coupled to the indicator for wirelessly transmitting information relating to the amount of collected blood to a receiver. In such embodiments, the receiver may be communicatively coupled to a display device configured to display information relating to the amount of collected blood.

Collection Bottle 160 may be constructed of glass, plastic, or other suitable materials. In some embodiments, Collection Bottle 160 may be implemented using one of BD's BACTEC™ culture vials or one of BD's Vacutainer® blood collection tubes. In some embodiments, Collection Bottle 160 may contain liquids and/or solid additives, such as a bacterial growth media, an antibiotic scavenger, or a pH sensor. In some embodiments, Collection Bottle 160 may contain one of BD's blood culture medias, such as BD's BACTEC™ Peds Plus™ medium, BD's BACTEC™ Plus Aerobic medium, BD's BACTEC™ Plus Anaerobic medium, BD's BACTEC™ Lytic Anaerobic medium, BD's BACTEC™ Standard Aerobic medium, or BD's BACTEC™ Standard Anaerobic medium.

As mentioned above, most organisms identified as contaminants in blood cultures originate from the skin of the patient. These contaminants are typically introduced into a patient's blood sample by the venipuncture and the initial flow of blood from the patient into a collection bottle. In the blood collection system of FIG. 1, the initial flow of blood is diverted and trapped in the diversion chamber of Diversion Device 140. As a result, the blood collection system of FIG. 1, provides a means for potentially reducing the number of false positive blood cultures. Moreover, the inclusion of Diversion Device 140 in the blood collection system of FIG. 1, does not introduce additional workflow steps for health care workers relative to presently conventional techniques for collecting blood samples. For example, health care workers do not need to wait for a conduit or a chamber to partially or completely fill before inserting Collection Bottle 160 into Holder 150.

Figure 2:
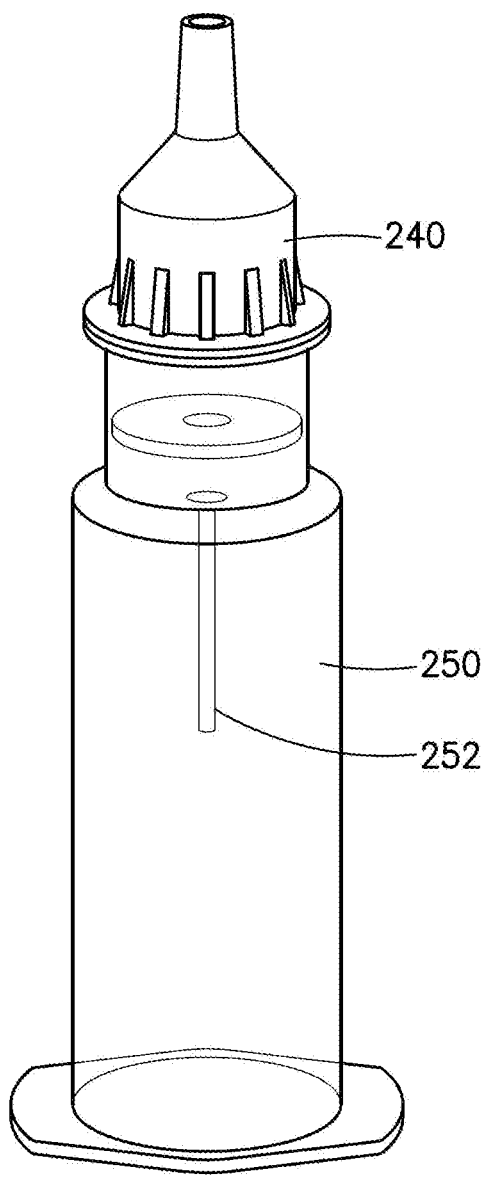
FIG. 2 illustrates an embodiment of a diversion device that is integrated with a holder in accordance with the present technology.

FIG. 2 illustrates an embodiment of a diversion device that is integrated with a holder in accordance with the present technology. As shown in FIG. 2, Diversion Device 240 is integrated with Holder 250, which includes Needle 252. Moreover, in this particular embodiment, Diversion Device 240 is configured to direct 1 mL of blood into its diversion chamber.

Figure 3A:
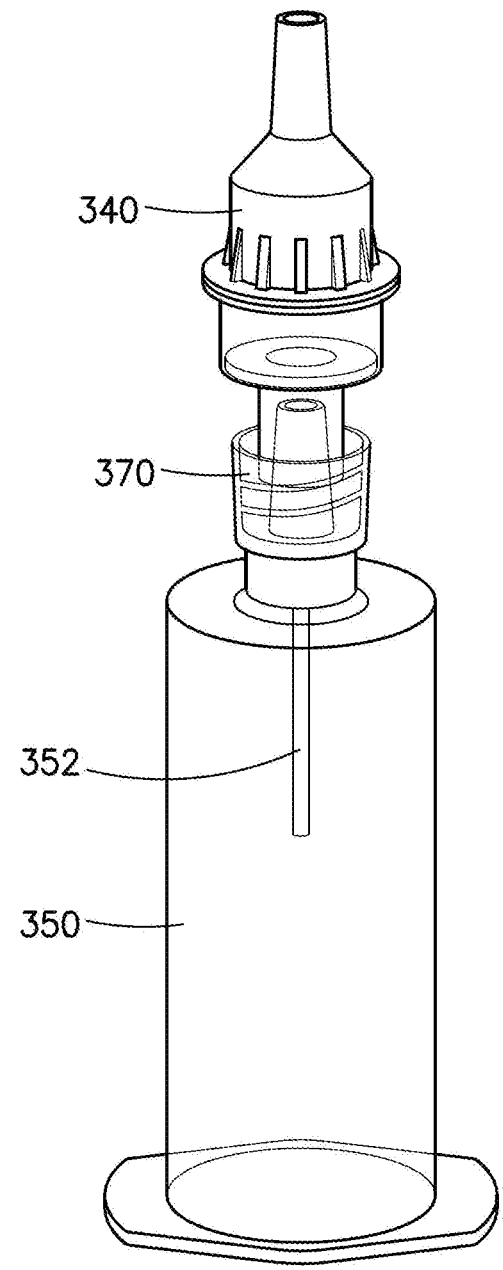
FIG. 3A illustrates an embodiment of a diversion device that can interface with a holder through an adapter in accordance with the present technology.

In contrast, FIG. 3A illustrates an embodiment of a diversion device that can interface with a holder through an adapter in accordance with the present technology. As shown in FIG. 3A, Diversion Device 340 is connected to Holder 350 through Adapter 370. Holder 350 includes Needle 352. Moreover, in this particular embodiment, Diversion Device 340 is configured to direct 0.5 mL of blood into its diversion chamber.

Figure 3B:
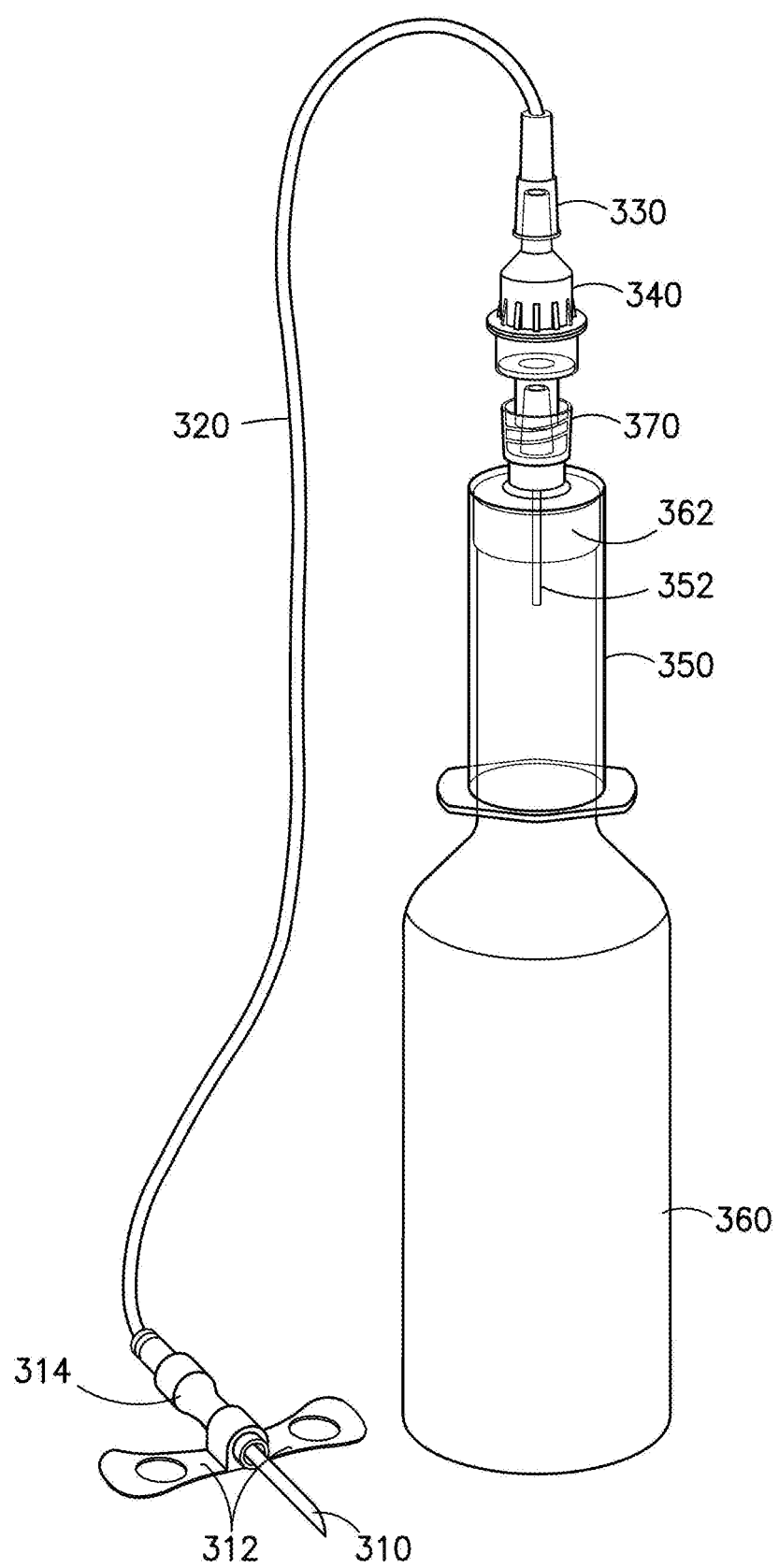
FIG. 3B illustrates a blood collection system comprising the diversion device illustrated in FIG. 3A.

FIG. 3B illustrates a blood collection system comprising the diversion device illustrated in FIG. 3A. As shown in FIG. 3B, the blood collection system includes Needle 310, Tubing 320, Adapters 330 and 370, Diversion Device 340, Holder 350, and Collection Bottle 360. Collection Bottle includes Cap 362. As shown, Needle 352 has pierced through Cap 362. During the process of collecting a blood sample from a patient, Needle 310 is used to pierce a vein or an artery of the patient. Driven by the vacuum pressure created by Collection Bottle 360, blood from the patient is directed toward Collection Bottle 360 through Tubing 320. An initial flow of blood passes through Adapters 330 and 370 and is trapped in a diversion chamber within Diversion Device 340. A subsequent flow of blood is collected in Collection Bottle 360. Along the way, the subsequent flow of blood passes through Adapters 330 and 370, Diversion Device 340, and Needle 352 of Holder 350.

As shown in FIG. 3B, Needle 310 includes Wings 312 and Body 314. Wings 312 can make it easier for a health care worker to grasp Needle 310. However, in other embodiments of the present invention, Wings 312 can be omitted. In some embodiments, Wings 312 may be constructed of a flexible plastic material. Body 314 may provide a health care worker with an indication that the vein or artery of a patient has been successfully pierced. For example, Body 314 may be constructed of a translucent plastic material that allows a health care worker to see an initial flash of blood from a patient. In other embodiments, Body 314 may be constructed of a transparent material or include a window. In some embodiments, the blood collection system of FIG. 3B may be implemented, in part, by using BD's Vacutainer® push button blood collection set in combination with one of BD's BACTEC™ culture vials.

Figure 4A:
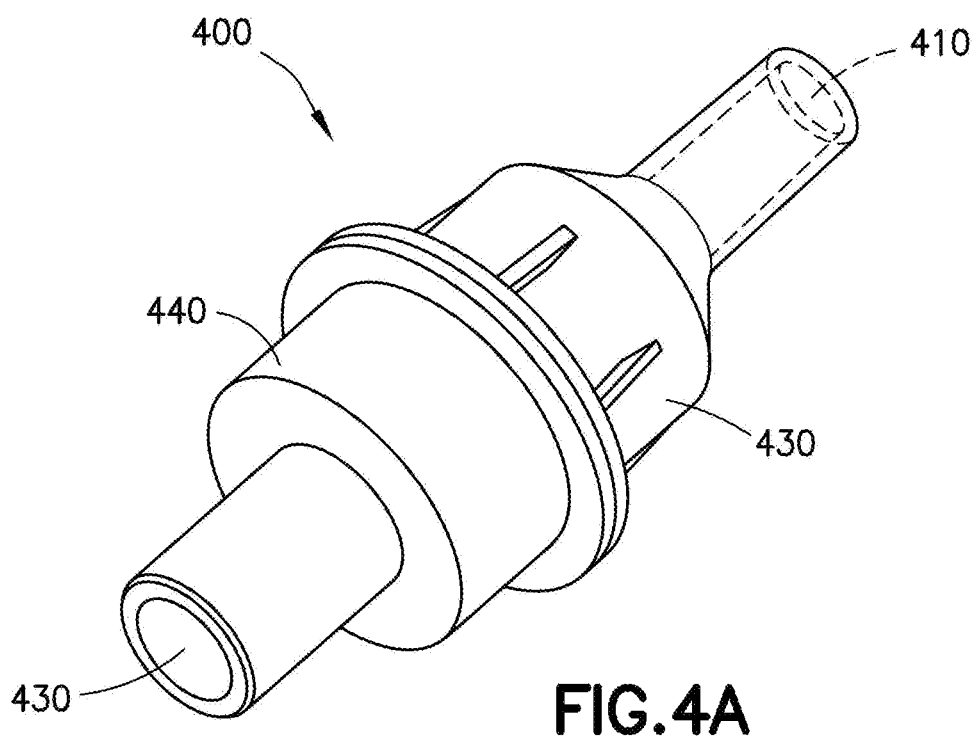
FIG. 4A illustrates an embodiment of a diversion device in accordance with the present technology.
Figure 4B:
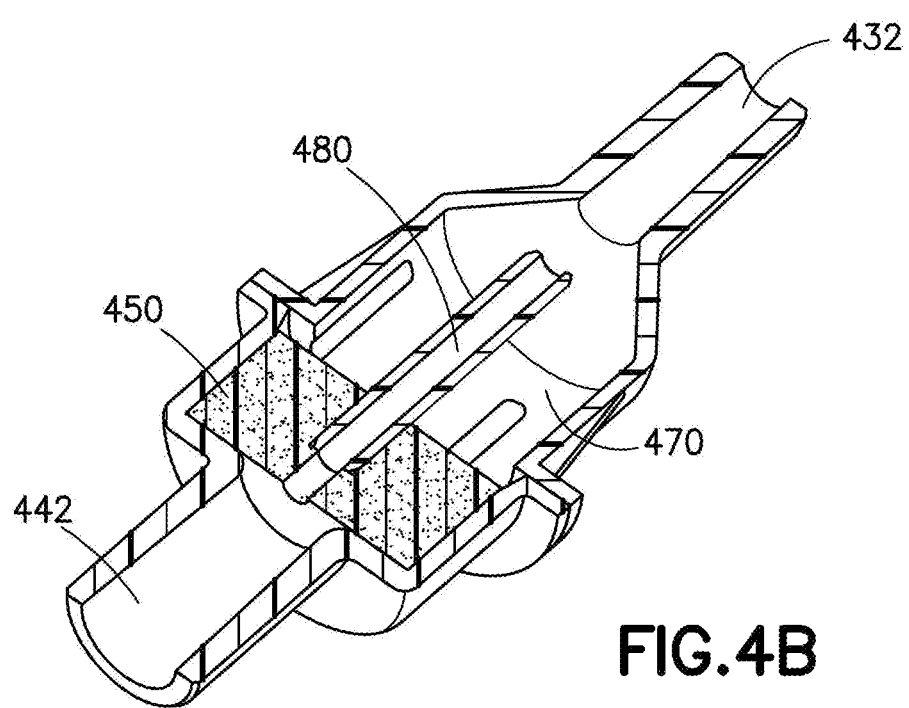
FIG. 4B is a cross-sectional view of the diversion device of FIG. 4A.

FIG. 4A illustrates an embodiment of a diversion device in accordance with the present technology. FIG. 4B is a cross-sectional view of the diversion device of FIG. 4A. FIG. 4C is an exploded diagram of the cross-sectional view of FIG. 4B. As shown in FIGS. 4A-C, Diversion Device 400 includes Inlet 410, Outlet 420, Housing Shell 430, Housing Base 440, Filter 450, and Tube 460. A portion of Housing Shell 430 forms Inlet Conduit 432. Similarly, a portion of Housing Base 440 forms Outlet Conduit 442. Another portion of Housing Base 440 forms Filter Receptacle 444, which generally conforms to the size and shape of Filter 450. As shown in FIG. 4B, Filter 450 rests inside of Filter Receptacle 444. Filter 450 includes Filter Conduit 454 and Tube Receptacle, which generally conforms to the size and shape of Tube 460. As shown in FIG. 4B, Tube 460 rests inside of Tube Receptacle 452. Collectively, Filter Conduit 454 and Tube 460 form Internal Conduit 480. Similarly, Diversion Chamber 470 is a chamber surrounding Tube 460, which is defined by portions of Housing Shell 430, Housing Base 440, and Filter 450.

When Diversion Device 400 is used as part of a blood collection system, blood from a patient flows into Inlet 410 and through Inlet Conduit 432. An initial flow of blood flows preferentially into Diversion Chamber 470. Diversion Chamber 470 is sized relative to the diameter of Internal Conduit 480 so that the initial flow of blood will more readily flow into Diversion Chamber 470 than into Internal Conduit 480. As blood collects in Diversion Chamber 470, blood will begin to flow into Internal Conduit 480 and out of Outlet 420 through Outlet Conduit 442.

In some embodiments, Housing Shell 430 and/or Housing Base 440 may be constructed of a hydrophilic material. For example, in some embodiments, Housing Shell 430 and/or Housing Base 440 may be constructed of a plastic material, such as Acrylonitrile Butadiene Styrene ("ABS"). In some embodiments, Tube 460 may be constructed of a hydrophobic material. For example, in some embodiments, Tube 460 may be constructed of a plastic material, such as Polyethylene. In some embodiments, Filter 450 may be constructed of a hydrophilic material. In some embodiments, Filter 450 may be constructed of a material that allows air to pass through, but not blood. For example, in some embodiments, Filter 450 may be constructed of a sintered porous polymer that absorbs liquid and swells. For example, Filter 450 may be constructed of a cellulose material, such as carboxymethylcellulose ("CMC"). In some embodiments, Housing Shell 430 may be attached to Housing Base 440 by an ultrasonic welding process. In some embodiments, Filter 450 may be inserted into Filter Receptacle 444 and/or Tube 460 may be inserted into Tube Receptacle 452 by a press fitting process.

Figure 5C:
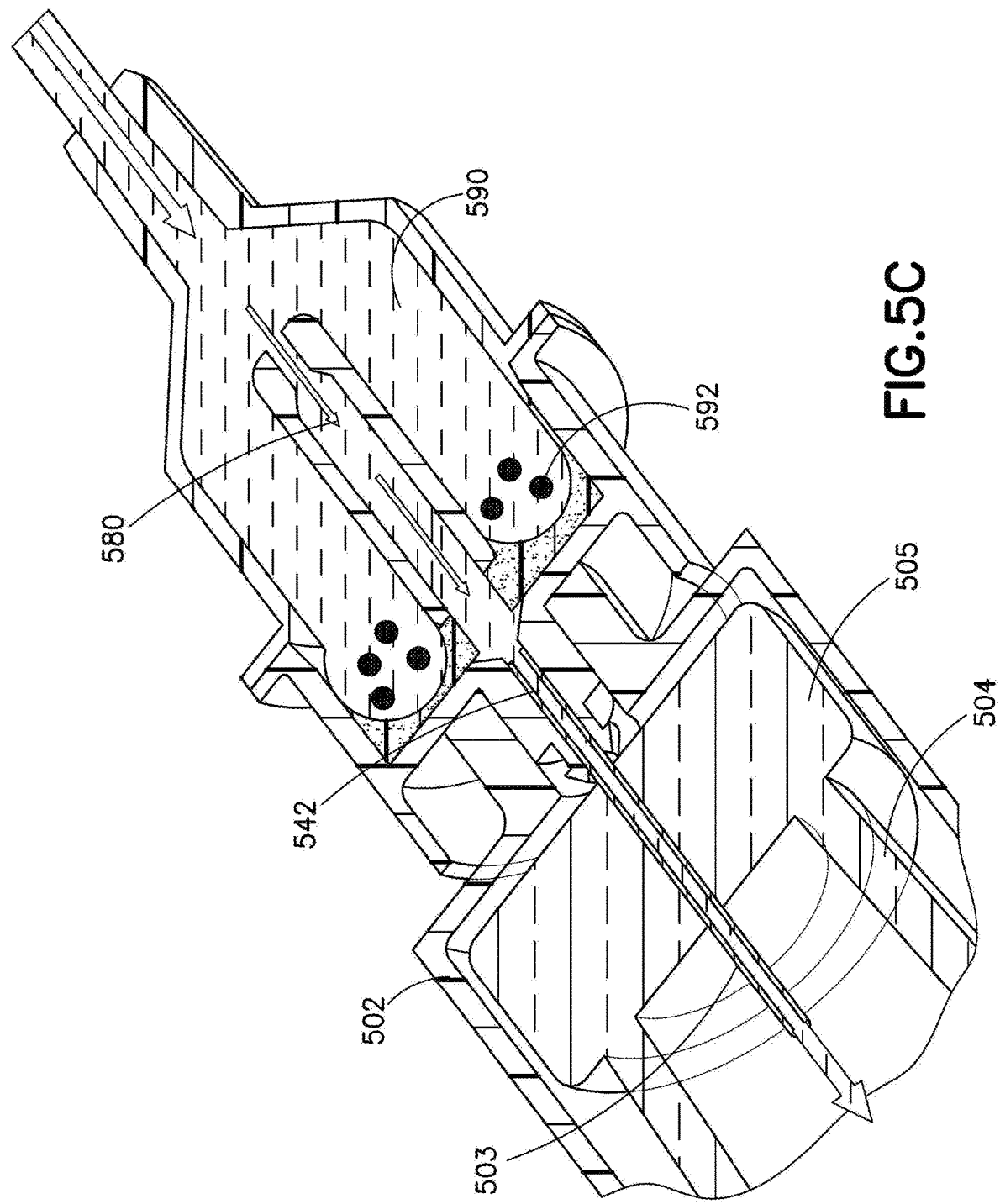
FIG. 5C illustrates how a subsequent flow of blood may flow through the internal conduit of the diversion device of FIG. 5A towards a collection bottle.

Collectively, FIGS. 5A-C illustrate how initial and subsequent flows of blood from a patient may flow through a diversion device in accordance with the present technology. As shown in FIGS. 5A-C, Diversion Device 500 includes Housing Shell 530, Housing Base 540, Filter 550, and Tube 560. A portion of Housing Shell 530 forms Inlet Conduit 532. Similarly, a portion of Housing Base 540 forms Outlet Conduit 542. Collectively, a portion of Filter 550 and Tube 560 form Internal Conduit 580. Similarly, Diversion Chamber 570 is a chamber surrounding Tube 560, which is defined by portions of Housing Shell 530, Housing Base 540, and Filter 550. As shown in FIGS. 5A-C, Diversion Device 500 is integrated with Holder 502. Furthermore, as shown, Needle 503 of Holder 502 is piercing Cap 505 of Collection Bottle 504.

FIG. 5A illustrates how an initial flow of Blood 590 from a patient may flow into Diversion Chamber 570. As shown in FIG. 5A, the initial flow of Blood 590 contains Bacteria 592. Moreover, the width of Diversion Chamber 570 is larger than the width of Inlet Conduit 532. Therefore, Diversion Chamber 570 has a lower resistance to blood flow than Inlet Conduit 532. As a result, when the initial flow of Blood 590 enters Diversion Chamber 570, it travels along the walls of Housing Shell 530 and avoids Tube 560. To further facilitate this behavior, Housing Shell 530 may be constructed of a hydrophilic material and Tube 560 may be constructed of a hydrophobic material. Furthermore, an inlet conduit of Tube 560 may have a width that is smaller than the width of Inlet Conduit 532.

FIG. 5B illustrates how an initial flow of Blood 590 from the patient may begin to fill Diversion Chamber 570. As mentioned above, a portion of Diversion Chamber 570 is defined by Filter 550. As shown in FIG. 5B, Filter 550 is constructed of a material that allows air to pass through it, but not blood. The air travels though Outlet Conduit 442. As such, Diversion Device 500 is a closed system. The initial flow of air through Diversion Device 500 is not vented to the atmosphere. Therefore, a health care worker does not need to wait for the air to be purged from Diversion Device 500 before connecting it to Collection Bottle 504. As a result, the initial flow of Blood 590 pushes air from Diversion Chamber 570 into Collection Bottle 504 through Filter 550. Furthermore, when the initial flow of Blood 590 first contacts Filter 550, some of it is absorbed by Filter 550. The portion of the initial flow of Blood 590 that is absorbed by Filter 550 becomes locked in place as Filter 550's microstructure swells. Advantageously, this portion of the initial flow of Blood 590 likely contains the most contaminants (e.g., Bacteria 592). As Filter 550 is wetted by the blood, it closes off the flow therethrough.

FIG. 5C illustrates how a subsequent flow of Blood 590 from the patient may flow through Internal Conduit 580 towards Collection Bottle 504. In some embodiments, the geometrical dimensions of Diversion Chamber 570 and Tube 560 may be selected such that within the range of applicable flow velocities, the flow of Blood 590 is laminar, so that the initial flow of Blood 590 with Bacteria 592, which is trapped in Diversion Chamber 570, remains undisturbed by the subsequent flow of Blood 590 through Diversion Device 500.

Figure 6A:
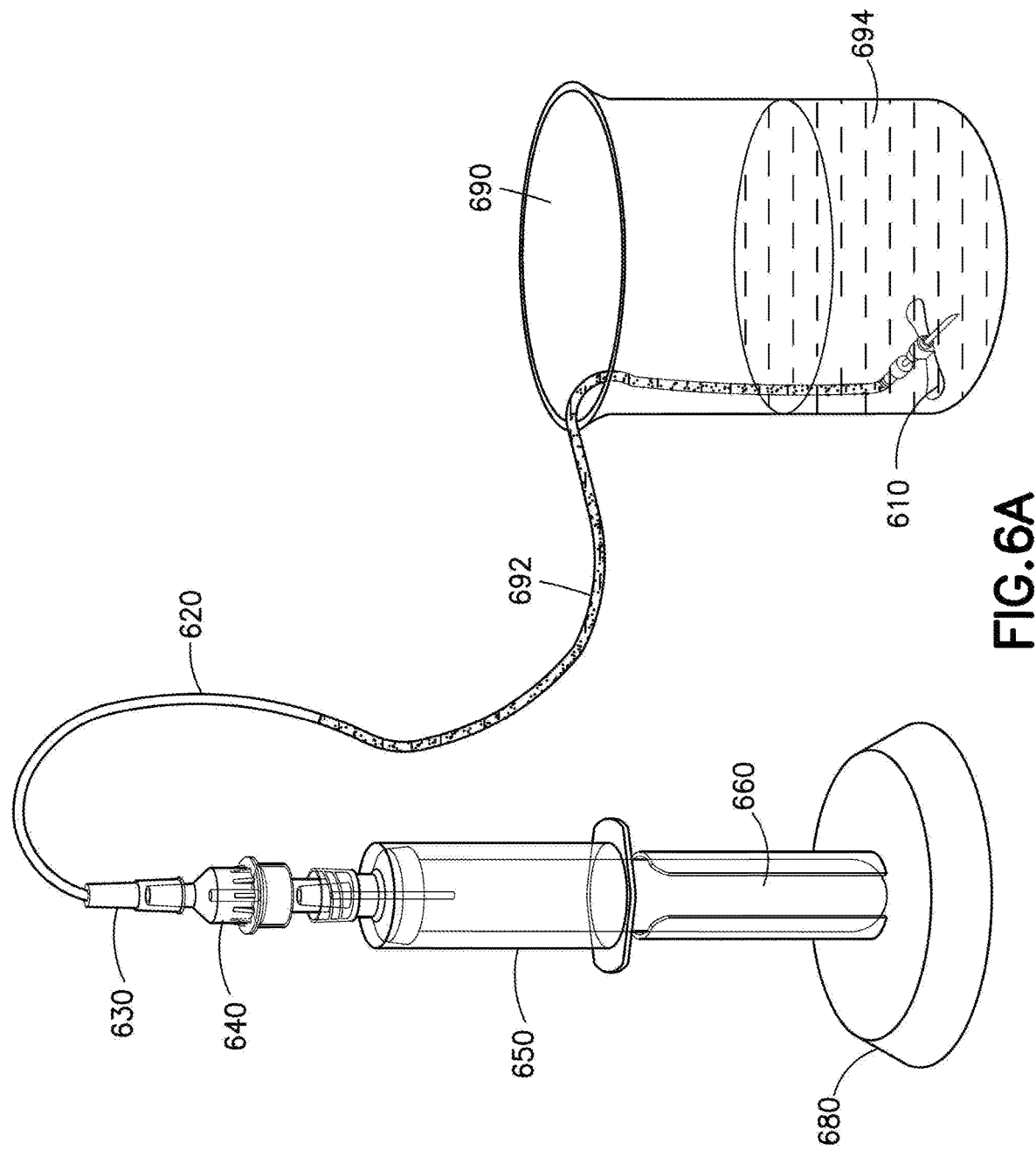
FIG. 6A is an illustration of the beginning of an experiment involving a prototype of a diversion device in accordance with the present technology.
Figure 6B:
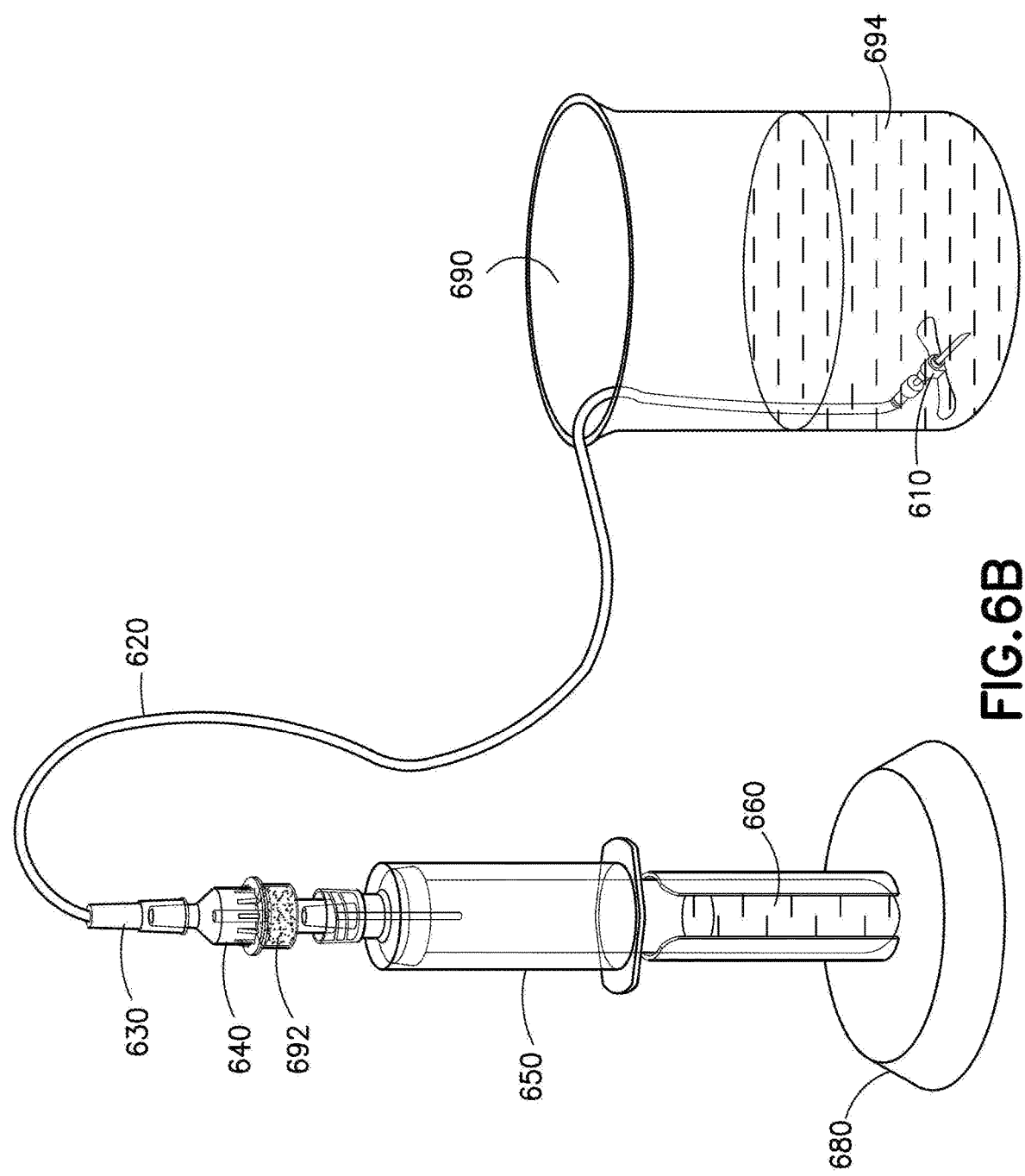
FIG. 6B is an illustration of the end of an experiment involving a prototype of a diversion device in accordance with the present technology.

FIGS. 6A-B are illustrations of the beginning and ending of an experiment involving a prototype of a diversion device in accordance with the present technology. As shown in FIGS. 6A-B, the blood collection system includes Needle 610, Tubing 620, Adapter 630, Diversion Device 640, Holder 650, Collection Bottle 660, and Stand 680. In this experiment, Stand 680 provides support for portions of the blood collection system. As shown in FIG. 6A, at the beginning of the experiment, Tubing 620 is filled with approximately 1 mL of Colored Liquid 692. Furthermore, at this point in time, a diversion chamber of Diversion Device 640 and Collection Bottle 660 are empty.

As shown in FIG. 6A, Needle 610 has just been then placed in Container 690, which contains Clear Liquid 694. Driven by the vacuum pressure created by Collection Bottle 660, Colored Liquid 692 then passes through Adapter 630 and is trapped in the diversion chamber within Diversion Device 640. Clear Liquid 694 subsequently flows into Collection Bottle 660. Along the way, Clear Liquid 694 passes through Adapter 630, Diversion Device 640, and a needle of Holder 650.

As shown in FIG. 6B, Colored Liquid 692 has been trapped in the diversion chamber of Diversion Device 640 and Collection Bottle 660 is filled with some of Clear Liquid 694. At the end of the actual experiment, a very small amount of Colored Liquid 692, which was barely discernable by the naked eye, flowed into Collection Bottle 660. Thus, Collection Bottle 660 was almost entirely filled with Clear Liquid 694. This experiment visually demonstrated the ability of Diversion Device 640 to trap an initial flow of a liquid and to permit a subsequent flow of that liquid into Collection Bottle 660. Moreover, the clarity of the liquid in Collection Bottle 660 at the end of the experiment demonstrated the effectiveness of Diversion Device 640.

As demonstrated above, some embodiments of the present invention provide significant advantages. Most organisms identified as contaminants in blood cultures originate from the skin of the patient. These contaminants are typically introduced into a patient's blood sample by the venipuncture and the initial flow of blood from the patient into a collection bottle. Therefore, by diverting and trapping an initial flow of blood, a diversion device in accordance with the present technology can potentially reduce the number of false positive blood cultures.

Furthermore, a diversion device in accordance with the present technology provides a versatile solution. For example, the size of a diversion chamber within a diversion device can be readily changed, so that any predetermined amount of blood in the range of about 0.05 mL to 3 mL can be diverted and trapped.

Moreover, the inclusion of a diversion device in accordance with the present technology in a blood collection system, does not introduce additional workflow steps for health care workers relative to presently conventional techniques for collecting blood samples. For example, health care workers do not need to wait for a conduit or a chamber to partially or completely fill before inserting a collection bottle into a holder. This advantage is achieved, in large part, because some embodiments of a diversion device in accordance with the present technology operate using the vacuum pressure created by a collection bottle. As a result, some embodiments of a diversion device in accordance with the present technology do not rely on a separate power source or the venous pressure of a patient for trapping an initial flow of blood or for collecting a subsequent flow of blood in a collection bottle.

As noted above, some embodiments of a blood collection system with a diversion device in accordance with the present technology represent closed system solutions. In these embodiments, the bolus of air that precedes the liquid blood flow is not vented out of the system and into the atmosphere. Instead, these embodiments use the vacuum pressure created by a collection bottle to immediately draw blood from a patient. A filter in these embodiments can be used inside the closed system to balance pressure and air flow along the flow path. For example, a filter can be used to allow a bolus of air to flow out of the diversion chamber and into an outlet conduit. In such embodiments, the filter may prevent flow therethrough after the filter is wetted by a liquid such as blood.

From the foregoing and with reference to the various figure drawings, those skilled in the art will appreciate that certain modifications can also be made to the present disclosure without departing from the scope of the same. For example, a diversion device in accordance with the present technology can be positioned anywhere along the flow path. For example, a diversion device in accordance with the present technology could be attached to the body of a needle. As another example, a diversion device in accordance with the present technology could be positioned along tubing between a holder and a needle.

Furthermore, a blood collection system in accordance with the present technology may not include all of the components illustrated in the above embodiments. For example, the needle, the diversion device, and the holder may be integrated into one device without any tubing. For example, a diversion device in accordance with the present technology could be integrated into BD's Vacutainer® Eclipse™ blood collection needle.

Moreover, in many of the embodiments discussed above, collection bottles having a sub-atmospheric internal pressure were used to collect blood from a patient. However, a wide variety of collection vessels having a sub-atmospheric internal pressure may be used with the present technology. For example, a collection tube may be used with the present technology. As another example, a collection vial may be used with the present technology.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A diversion device comprising:
   a housing having an inlet conduit and an outlet conduit, wherein the housing is configured to receive an initial flow of blood and a subsequent flow of blood through the inlet conduit, and wherein the housing is configured to allow the subsequent flow of blood to exit the diversion device through the outlet conduit;
   a filter positioned within the housing adjacent to the outlet conduit, wherein the filter comprises a material that allows air, but not blood, to pass through it;
   a diversion chamber defined by portions of the housing and the filter, wherein the diversion chamber is configured to receive and retain the initial flow of blood; and
   an internal conduit positioned within the housing, the internal conduit including a tube having a first end extending through the filter and a second end extending into the diversion chamber, wherein the internal conduit is configured to permit the subsequent flow of fluid to exit the diversion device.

2. The diversion device of claim 1, wherein a portion of the housing comprises a hydrophilic material.

3. The diversion device of claim 2, wherein a portion of the internal conduit comprises a hydrophobic material.

4. The diversion device of claim 3, wherein a cross-sectional area of the diversion chamber is larger than a cross-sectional area of the internal conduit.

5. The diversion device of claim 1, wherein the first end of the internal conduit is a conduit formed in the filter, and wherein the first end of the tube is positioned within a tube receptacle formed in the filter.

6. The diversion device of claim 5, wherein the housing comprises a housing shell and a housing base, wherein the housing shell contains the inlet conduit, wherein the housing base contains the outlet conduit, and wherein the filter is positioned within a filter receptacle formed in the housing base.

7. The diversion device of claim 6, wherein the filter comprises a hydrophilic material.

8. The diversion device of claim 7, wherein the hydrophilic material is carboxymethylcellulose ("CMC").

9. The diversion device of claim 1, wherein a vacuum pressure created by a collection vessel coupled to the diversion device draws the initial flow of blood into the diversion chamber.

10. The diversion device of claim 9, wherein the internal conduit is configured to permit the subsequent flow of fluid to exit the diversion device using only the vacuum pressure created by the collection vessel coupled to the diversion device.

11. A blood collection kit comprising:
    instructions to assemble a blood collection pathway from a patient to a collection vessel,
    wherein the blood collection pathway comprises a first needle piercing the skin of the patient and the diversion device of claim 1, and
    wherein the collection vessel has a sub-atmospheric internal pressure that draws (a) an initial flow of blood from the patient through the first needle and into the diversion device and (b) a subsequent flow of blood through the first needle and the diversion device, respectively, and into the collection vessel, and
    wherein the blood collection pathway is a closed system that prevents an initial flow of air through the diversion device of claim 1 from being vented into the atmosphere.

12. The blood collection kit of claim 11, wherein the blood collection pathway further comprises a holder having a second needle piercing a cap of the collection vessel.

13. The blood collection kit of claim 12, wherein the diversion device of claim 1 is integrated with the holder.

14. The blood collection kit of claim 12, wherein the diversion device of claim 1 and the holder are separate units.

15. The blood collection kit of claim 11, wherein the collection vessel contains one or more a bacterial growth media, an antibiotic scavenger, or a pH sensor.

16. A blood collection method comprising:
    assembling a blood collection pathway from a patient to a collection vessel,
    wherein the blood collection pathway comprises a first needle piercing the skin of the patient and a diversion device, and
    wherein the collection vessel has a sub-atmospheric internal pressure that draws (a) an initial flow of blood from the patient through the first needle and into the diversion device and (b) a subsequent flow of blood through the first needle and the diversion device, respectively, and into the collection vessel, and
    wherein the diversion device comprises:
       a housing having an inlet conduit and an outlet conduit, wherein the housing is configured to receive an initial flow of blood and a subsequent flow of blood through the inlet conduit, and wherein the housing is configured to allow the subsequent flow of blood to exit the diversion device through the outlet conduit;
       a filter positioned within the housing adjacent to the outlet conduit, wherein the filter comprises a material that allows air, but not blood, to pass through it;

a diversion chamber defined by portions of the housing and the filter, wherein the diversion chamber is configured to receive and retain the initial flow of blood; and an internal conduit positioned within the housing the internal conduit including a tube having a first end forming a conduit through the filter and a second end extending into the diversion chamber, wherein the internal conduit is configured to permit the subsequent flow of fluid to exit the diversion device.

17. The method of claim 16, wherein the blood collection pathway is a closed system that prevents an initial flow of air through the diversion device from being vented into the atmosphere.

18. The method of claim 16, wherein the blood collection pathway further comprises a holder having a second needle piercing a cap of the collection vessel.

19. The method of claim 18, wherein the diversion device is integrated with the holder.

20. The method of claim 18, wherein the diversion device and the holder are separate units.

\* \* \* \* \*